US005993848A

United States Patent [19]

Suzuki et al.

[11] Patent Number: 5,993,848

[45] Date of Patent: Nov. 30, 1999

[54] DISSOLUTION LIQUID FOR DRUG IN IONTOPHORESIS

[75] Inventors: Yasuyuki Suzuki; Katsumi Iga, both of Suita; Yukihiro Matsumoto, Ikeda, all of Japan

[73] Assignee: Takeda Chemical Industries, Ltd., Osaka, Japan

[21] Appl. No.: 08/659,372

[22] Filed: Jun. 6, 1996

[30] Foreign Application Priority Data

| | | | |
|---|---|---|---|
| Jun. 9, 1995 | [JP] | Japan | 7-142983 |
| Aug. 8, 1995 | [JP] | Japan | 7-201902 |

[51] Int. Cl.[6] A61K 31/785; A61F 13/00

[52] U.S. Cl. 424/449; 424/484

[58] Field of Search 424/449, 484, 424/78.03, 78.1, 78.16; 128/639, 640, 644; 604/20

[56] References Cited

U.S. PATENT DOCUMENTS

| | | | |
|---|---|---|---|
| 4,593,053 | 6/1986 | Jevne et al. | 523/111 |
| 5,135,480 | 8/1992 | Bannon et al. | 604/20 |
| 5,158,537 | 10/1992 | Haak et al. | 604/20 |
| 5,527,797 | 6/1996 | Eisenberg et al. . | |

FOREIGN PATENT DOCUMENTS

| | | |
|---|---|---|
| 0 643 981 | 3/1995 | European Pat. Off. . |
| 5-32696 | 2/1993 | Japan . |
| 06016535 | 1/1994 | Japan . |
| 6-16538 | 1/1994 | Japan . |
| 90/08571 | 8/1990 | WIPO . |
| WO 92/04938 | 4/1992 | WIPO . |
| 93/10163 | 5/1993 | WIPO . |
| 93/25168 | 12/1993 | WIPO . |

OTHER PUBLICATIONS

Pharmazie 49, 1994.

*Primary Examiner*—Thurman K. Page
*Assistant Examiner*—Kathryne E. Shelborne
*Attorney, Agent, or Firm*—Wenderoth, Lind & Ponack, LLP

[57] ABSTRACT

A drug held or supported by an interface comprising a porous matrix is dissolved with a drug dissolution liquid containing a humectant, and the drug is transdermally delivered by iontophoresis. The humectant includes e.g. glycerin and other polyhydric alcohols, sugar alcohols, proline and other amino acids and acidic mucopolysaccharides. The concentration of the humectant may be about 1 to 50% by weight, and the concentration of proline or other amino acid or its salt may be about 1 to 30% by weight. The drug includes (1) a physiologically active peptide or protein with a molecular weight of 100 to 30,000 or (2) a nonpeptide physiologically active compound with a molecular weight of 100 to 1,000.

16 Claims, 3 Drawing Sheets

F I G. 1
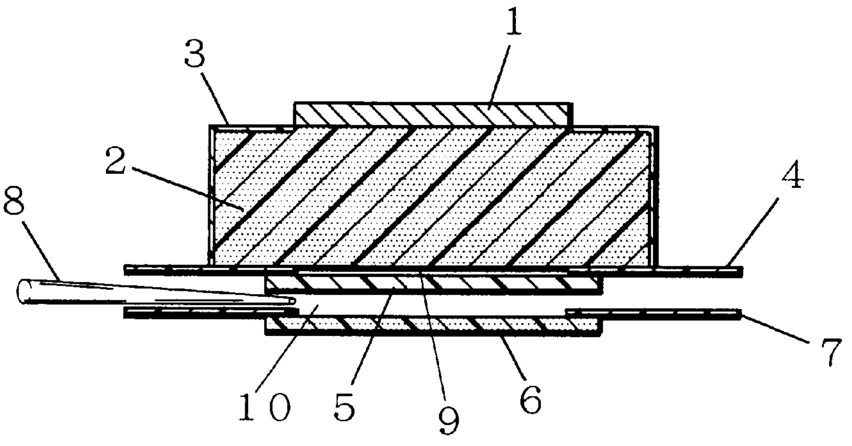
F I G. 2
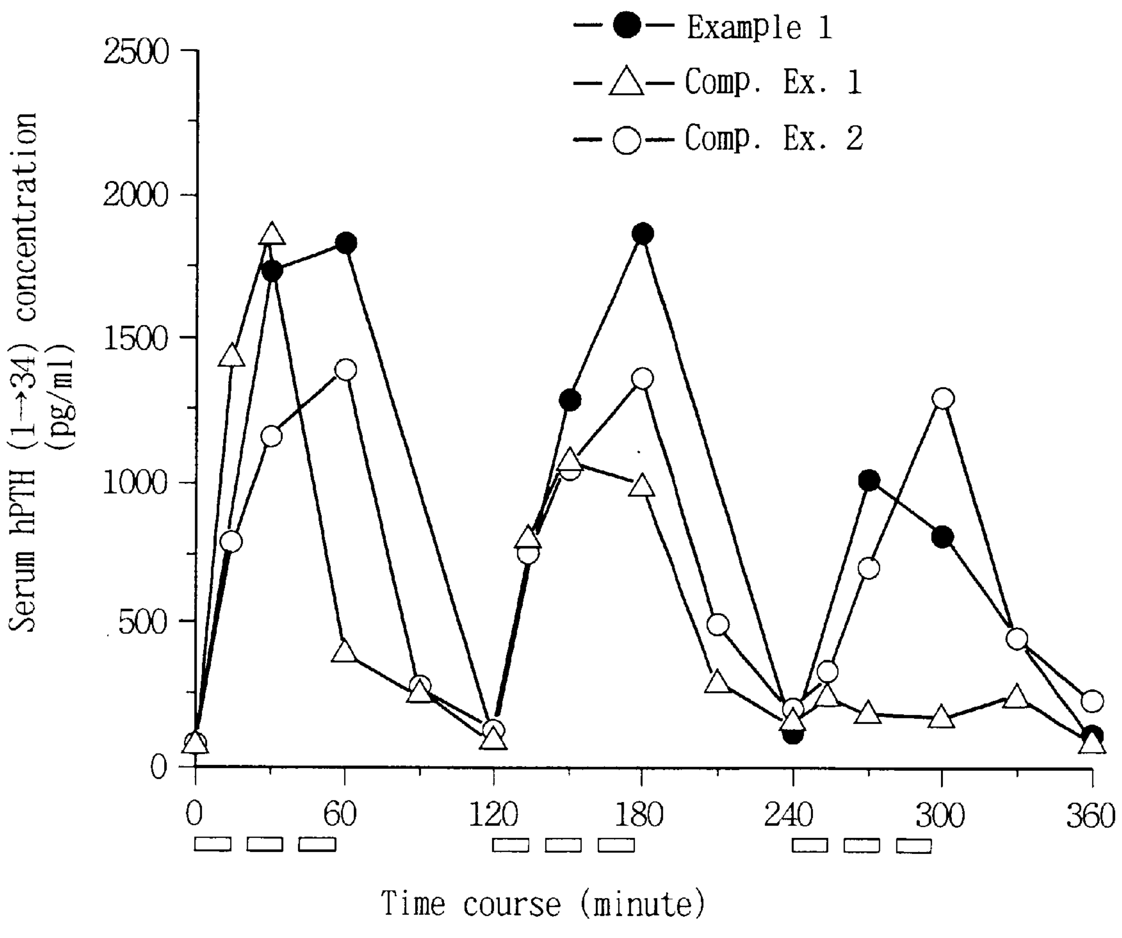

DISSOLUTION LIQUID FOR DRUG IN IONTOPHORESIS

BACKGROUND OF THE INVENTION

1. Field of the Invention

This invention relates to a dissolution liquid for a drug in iontophoresis which is useful for dissolving a drug in an interface (a skin contactor or patch) for iontophoresis and delivering the drug transdermally, and a method for promoting transdermal or percutaneous absorption of the drug with the use of the dissolution liquid.

2. Description of Related Art

Iontophoresis is a system for promoting or accelerating transdermal absorption (endermic absorption) with the use of electricity as an external stimulus. The principle of such iontophoresis basically resides in promoting or enhancing transmittance of a drug molecule through a skin barrier due to, in an electric field between an anode and a cathode produced by an electric current, moving force of a positively charged molecule from the anode to the cathode, and a moving force of a negatively charged molecule from the cathode to the anode [see Journal of Controlled Release, 18, 213–220 (1992); Advanced Drug Delivery Review, 9, 119 (1992); and Pharmaceutical Research, 3, 318–326 (1986)].

Recent advances of synthetic technologies and genetic engineering insure pure and mass production of a naturally-occurring peptide or protein, or a peptide or protein in which the amino acid composition of the naturally-occurring peptide or protein is changed, or a chemically-modified derivative thereof. Therefore, application of these peptides or proteins as drugs (medicaments) have been desired. On the other hand, it has been recognized that various physiological activities are physiologically controlled by delicate and complicated in vivo kinetics with advanced researches for these peptides or proteins. Therefore, a system capable of corresponding to a strict control of administration (dosage) of these peptides or proteins is required for exhibition of the maximum drug effect in a specific disease and minimizing a side effect (adverse reaction).

By way of illustration, a calcitonin has an activity of inhibiting (suppressing) decrease of the amount of a bone by means of inhibiting bone resorption, and hence is used for treatment (therapy) of osteoporosis, Paget's disease or other diseases. Although an excessive administration of the calcitonin causes a side effect such as anorexia (inappetence), frequent administration (frequent dosage), that is, repeated administration of the calcitonin is required for promoting therapeutic effects for the disease. Further, some peptides exhibit different drug effects depending on a medication process. Taking parathyroid hormone as an example, it has been known that the parathyroid hormone has incompatible effects or activities of deossification activity and ossification promoting activity, and the deossification activity is strongly exhibited when the hormone is administered by intravenous injection at a slow rate, and ossification promoting activity is clearly expressed when the hormone is administered by frequent hypodermic injections. Accordingly, when the parathyroid hormone is used as a therapeutical drug for osteoporosis in expectation of its ossification activity, a pharmaceutical preparation comprising the hormone should be not a sustained releasable preparation but a pulse-releasable preparation.

However, such physiologically active peptide or protein is generally decomposed by a digestive fluid or juice in a gastrointestinal tract (digestive tract) or hydrolyzed by a hydrolase present in the digestive tract wall, and hence absorption efficiency of the peptide or protein can hardly be improved effectively. Therefore, sufficient drug effect of such physiologically active peptide or protein is not expected by oral administration, and it is usually administered by an injection. Administration as an injectable preparation, however, causes a great pain to a patient and burdens him with a heavy load since such injectable preparation can not be administered by himself. Still more, when repeated and continuous administration is required such as in the calcitonin or parathyroid hormone, the pain and burden of the patient are increased, particularly speaking.

In the field of pharmaceutical preparations, the iontophoresis is intensively researched as a new drug delivery system capable of corresponding to administration or delivery of such physiologically active peptide or protein. That is, development of a pharmaceutical preparation comprising a drug hitherto administrable only as an injection and being administrable by a patient himself with the use of the iontophoresis will provide a therapy at home. Further, an optional absorption pattern of a drug can be constructed by means of a precise control of an electric voltage or current application time (period). In particular, when the iontophoresis is applied supplemental therapy (treatment) of an endogenous compound in consideration of circadian rhythm of a living body, more effective therapy with it is expected to be realized.

In a drug delivery system (administration system) with the use of the iontophoresis having such advantages, an electrode for application of an electric current, a membrane holding or supporting a drug (an interface as a skin contactor or patch) which is conductible to the electrode and capable of making contact with a skin, and a reference electrode are generally employed. The drug supported by the drug-supporting membrane is dissolved with a drug dissolution liquid contained in a spacer capable of making contact with the drug-supporting membrane.

An interface for iontophoresis which comprises a drug-supporting membrane and a spacer containing a drug dissolution liquid is in a small size and has a high drug absorptivity. Use of the above interface, however, moisture content in a surface to be made contact with the skin and in the drug-supporting membrane is decreased due to transpiration or evaporation of the drug dissolution liquid during the application of the electric current, and hence electric conductivity (applicability of electric current) is deteriorated. Hence, the iontophoresis using an interface having such construction does not provide a satisfactorily sufficient transdermal drug delivery (drug absorption) with a prolonged application of the interface. Therefore, suppression of the transpiration of the dissolution liquid seems to ensure maintenance of the electric conductivity over a long period, and to provide sufficient transdermal drug delivery by means of iontophoresis.

WO 93/25168 discloses inhibition of an initial burst of transdermal absorption by using a transdermal absorbent (drug composition) containing a drug and 0.1 to 50% (v/v) of glycerin in a transdermal drug delivery system. This literature describes that the form of the drug composition is gel, cream or others, and the drug composition may comprise an adhesive for supporting the composition in a site to which the composition is applied.

WO 90/08571 discloses a drug layer of an interface for iontophoresis as produced with the use of a hard porous material or a gel, and water or a polyhydric alcohol such as glycerin as a softening plasticizer.

WO 93/10163 discloses a preparation process of a hydrophilic gel which comprises irradiating an aqueous composition comprising a crosslinkable water-soluble polymer such as a polyethylene oxide, about 1 to 40% by weight of a humectant such as glycerin or propylene glycol, and a crosslinking accelerator with a radiation. This literature also describes an application of the hydrophilic gel to a patch or an electrode assembly.

These literatures, however, fail to disclose the use of a polyhydric alcohol or an amino acid for inhibition of moisture in a dissolution liquid in the iontophoresis. Further, the use of such drug composition, drug layer or hydrophilic gel for transdermal drug administration by iontophoresis may occasionally result in an increased skin irritation accompanied with the application of an electric current.

SUMMARY OF THE INVENTION

It is, therefore, an object of the present invention to provide a drug dissolution liquid which is useful for inhibiting transpiration of moisture from the drug dissolution liquid and hence maintaining electric conductivity (applicability of an electric current) over a long period of time.

It is another object of the invention to provide a drug dissolution liquid which is advantageous for transdermal drug absorption with a high bioavailability and an excellent reproducibility.

A further object of the invention is to provide a drug dissolution liquid which ensures mitigation of a skin irritation accompanied with application of an electric current in the iontophoresis.

It is yet another object of the invention to provide an interface for iontophoresis and a drug delivery system with the use of the above-mentioned drug dissolution liquid.

A still further object of the invention is to provide a method for promoting transdermal absorption of a drug which promotes transdermal absorption of a drug held or supported by an interface with efficacy and certainty.

The inventors of the present invention made intensive investigation to accomplish the above objects and found that incorporation of a humectant into a drug dissolution liquid in an interface for iontophoresis ensures long-term maintenance of conductivity (applicability of an electric current) and provides transdermal administration of a drug with a remarkably high bioavailability and excellent reproducibility. The present invention has been accomplished on the basis of the above findings and further investigation.

Thus, (1) the drug dissolution liquid of the present invention is a dissolution liquid for transdermal drug delivery by iontophoresis with the use of an interface comprising a porous matrix holding or supporting a drug, which comprises a humectant. The humectant may include at least one member selected from the group consisting of polyhydric alcohols, sugar alcohols, amino acids and acidic mucopolysaccharides. The polyhydric alcohol may for example be a polyhydric alcohol having 2 to 4 hydroxyl groups per molecule, such as glycerin. The amino acid may be an amino acid having a nitrogen-containing heterocycle such as a nonaromatic nitrogen-containing 5-membered heterocycle (e.g. proline, hydroxyproline). The concentration of the humectant may be selected within an adequate range, and the content of the polyhydric alcohol may be about 10 to 50% by weight, and the concentration of the amino acid may be about 1 to 30% by weight, typically speaking.

The drug (medicament or medicine) includes physiologically active peptides or proteins, or non-peptide physiologically active compounds.

The present invention also discloses (2) an interface for iontophoresis which comprises a porous matrix holding or supporting a drug, and a humectant, (3) a transdermal drug delivery (absorption) system which is provided with an interface capable of making contact with a skin and comprising a matrix holding or supporting a drug, a dissolution liquid for dissolving the drug containing a humectant, and a supply means for supplying the dissolution liquid to the interface for transdermal delivery of the drug dissolved with the dissolution liquid by means of iontophoresis. The matrix in the interface and the system may be a non-gel and porous matrix in the form of a sheet. The humectant may be held or supported at least in an area or region to which an electric current can be applied.

Further, the invention also discloses (4) an applicator which comprises an electrode to which an electric voltage can be applied, and an interface being conductible to the electrode, capable of making contact with a skin and holding or supporting a drug, wherein the applicator is capable of supplied with an aqueous solution containing a humectant for dissolution of the drug.

The present invention is useful as (5) a method for promoting transdermal absorption of a drug by an interface for iontophoresis which comprises holding or supporting a drug and a humectant at least in an area to which an electric current is applied.

It should be understood that the codes with respect to amino acids, peptides and so forth as used in the present specification are based on codes according to IUPAC-IUB Commission on Biochemical Nomenclature, or conventional codes used in the field of art. When there are optical isomers for an amino acid, the amino acid represents an L-form, otherwise specifically defined.

BRIEF DESCRIPTION OF THE DRAWINGS

FIG. 1 is a cross sectional view illustrating an embodiment of an applicator.

FIG. 2 is a graph showing changes of the concentration of hPTH (1→34) in the serum (sometimes referred to briefly as serum hPTH (1→34) concentration) during the time course (time passage) in Example 1, Comparative Example 1 and Comparative Example 2.

DETAILED DESCRIPTION OF THE INVENTION

Figure 3:
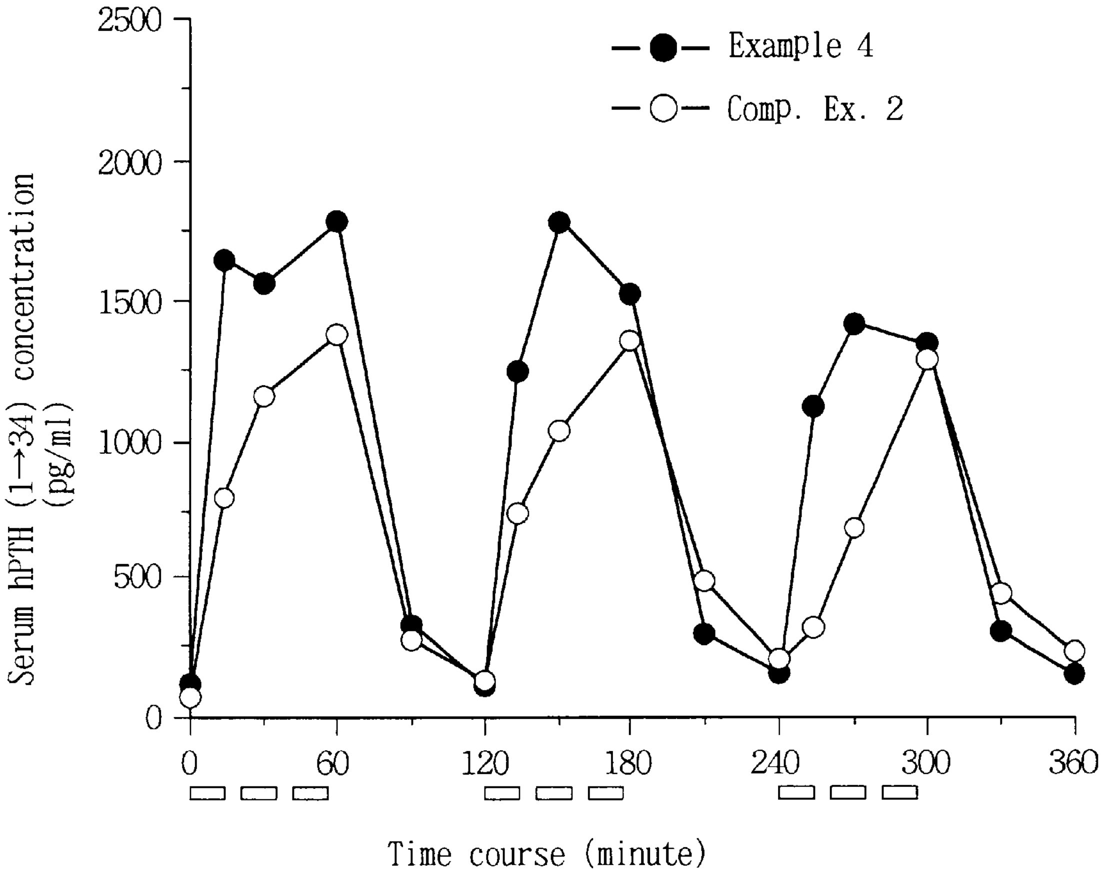
FIG. 3 is a graph showing changes of the serum hPTH (1→34) concentration during the time course in Example 4 and Comparative Example 2.

The present invention is now described in detail with referring to the drawings where necessary.

The humectant contained in the drug dissolution liquid of the invention is not particularly limited as far as being a substance which ensures inhibition of transpiration of moisture from the drug dissolution liquid, and provides maintenance or reservation of moisture (water) in the surface to be made contact with a skin and in the drug-supporter (drug-holder) in the interface, and which does not adversely affect on the skin. The humectant includes, for instance, (1) polyhydric alcohols, (2) sugar alcohols, (3) amino acids and (4) acidic mucopolysaccharides. These humectants may be used singly or in combination.

The polyhydric alcohol (1) includes, for example, glycerin, ethylene glycol, propylene glycol, 1,3-butylene glycol, pentaerythritol, polyethylene glycol, adducts in which ethylene oxide is added to these polyhydric alcohols (e.g. dioxyethylene glycol, trioxyethylene glycol, polyoxyethylene glycol, an ethylene oxide-propylene oxide copolymer, a glycerin-ethylene oxide adduct, a pentaerythritol-ethylene oxide adduct, etc.). Such polyhydric alcohols can be employed independently or in combination. Preferred examples of the polyhydric alcohol include polyhydric alcohols each having 2 to 4 hydroxyl group per molecule, in particular glycerin.

As the sugar alcohol (2), there may be mentioned for example xylitol and other pentitol, sorbitol, mannitol, galactitol and other hexitol. These sugar alcohols may also be used singly or in combination.

Examples of the amino acid (3) include (i) an amino acid constituting a protein, (ii) a naturally-occurring amino acid derived or obtained as a metabolite of a microorganism, or an animal or plant component, and (iii) an amino acid obtained by organic synthesis.

(i) The amino acid constituting a protein includes glycine, alanine, valine, leucine, isoleucine and other aliphatic monoaminomonocarboxylic acids; serine, threonine and other aliphatic hydroxyamino acids, aspartic acid, glutamic acid and other acidic amino acids; asparagine, glutamine and other acidic amino acid amides; phenylalanine, tyrosine, tryptophane and other aromatic amino acids; proline, hydroxyproline and other amino acids each having pyrrolidine ring; pyroglutamic acid (pyrrolidone-carboxylic acid) and other amino acids each having pyrrolidone ring; arginine, lysine, histidine and other basic amino acids; methionine, cystine, cysteine and other sulfur-containing amino acids, for instance. Such amino acids may be employed independently or in combination.

(ii) As the naturally-occurring amino acid derived or obtained as a metabolite of a microorganism or an animal or plant component, there may be mentioned, for example, L-α-aminobutyric acid, γ-aminobutyric acid, β-aminoisobutyric acid, β-alanine, homoserine, α-methyl-D-serine, O-carbamyl-D-serine, δ-hydroxy-γ-oxo-norvaline and other aliphatic monoaminomonocarboxylic acids; L-α-aminoadipic acid, L-β-aminoadipic acid, L-theanine, L-γ-methylene-glutamic acid, L-γ-methylglutamic acid and other monoaminodicarboxylic acids; L-ornithine, β-ly-sine, α,β-diaminopropionic acid, L-α,γ-diaminobutyric acid and other diaminomonocarboxylic acids; diaminopimeric acid and other diaminodicarboxylic acids; cysteic acid and other sulfonic acid-containing monoaminomonocarboxylic acids; taurine and other sulfonic acid-containing amino acids; kynurenine, 3,4-dioxyphenyl-L-alanine and other aromatic amino acids; 2,3-dicarboxyaziridine, [S]-2-amino-3-(isoxazolin-5-on-4-yl)-propionic acid, anticapsin and other heterocyclic amino acids; L-4-oxalysine, L-4-oxolysine, [3R,5R]-3,6-diamino-5-hydroxyhexanoic acid and other basic amino acids; lanthionine, S-methyl-L-cysteine and other sulfur-containing amino acids; pipecolic acid, azetidine-2-carboxylic acid, [1R,2S]-2-amino-cyclopentan-1-carboxylic acid and other cyclic amino acids; citrulline, alanosine, azaserine and other specific functional group-substituted amino acids and so forth.

Examples of (iii) the amino acid obtained by organic synthesis include trimethylglycine, 6-aminohexanoic acid, 8-aminooctanoic acid, 12-aminododecanoic acid and other aliphatic aminocarboxylic acids, 4-aminobenzoic acid, 4-(aminomethyl)benzoic acid, 4-(N-(carboxymethyl) aminomethyl)benzoic acid and other aromatic aminocarboxylic acids.

The amino acid may be used in the form of a salt. The salt of the amino acid includes, for example, a salt with a base [e.g. ammonia, alkali metals (e.g. sodium, potassium) and other inorganic basis, and trimethylamine, triethylamine and other organic basis], and a salt with an acid [hydrochloric acid, sulfuric acid, nitric acid, phosphoric acid and other inorganic acids, and acetic acid, propionic acid, p-toluenesulfonic acid and other organic acids].

Preferred amino acid includes amino acids each having a nitrogen-containing heterocycle (e.g. proline, hydroxyproline and other amino acids having pyrrolidine ring, pyrrolidonecarboxylic acid, histidine, tryptophane and other amino acids constituting a protein) or salts thereof, typically speaking. Among them, amino acids each having nonaromatic nitrogen-containing 5-membered heterocycle (e.g. amino acids each having pyrrolidine ring such as proline and hydroxyproline and pyrrolidonecarboxylic acid) or salts thereof can advantageously be employed.

(4) The acidic mucopolysaccharide includes, for instance, hyaluronic acid, chondroitin sulfate, and salts thereof [e.g. salts with alkali metals (e.g. sodium, potassium)].

Among these humectants, polyhydric alcohols (in particular glycerin) and amino acids or salts thereof (in especial, proline and other amino acids each having a nitrogen-containing heterocycle) may preferably be used. The use of the amino acid (in particular, proline and other amino acids each having a nitrogen-containing heterocycle) or its salt ensures remarkable mitigation of skin irritation accompanied with an electric current application, and provides an increased quantity of applied electricity in an application of an electric current succeeding to the first application of current in a case that transdermal absorption is conducted in plural times at periodic intervals, and hence ensures an improved transdermal absorptivity.

The content of the humectant in the drug dissolution liquid comprising an aqueous solution may be selected from a suitable range, according to the species of the humectant, which ensures suppression of transpiration of moisture from the drug dissolution liquid and reserves the moisture on the surface of the skin and in the drug-supporter (drug-holder). The content of the humectant is, for example, about 1 to 90% by weight, preferably about 1 to 80% by weight, and more preferably about 1 to 50% by weight based on the amount of the drug dissolution liquid. Among them, the amino acid and its salt ensures a high retention of moisture even used in a small amount. In more concretely, when the humectant is a polyhydric alcohol such as glycerin, the content of the humectant in the drug dissolution liquid is, for instance, about 5 to 50% by weight (e.g. about 10 to 50% by weight), and preferably about 20 to 40% by weight. When the humectant is the amino acid or its salt, the proportion of the humectant in the drug dissolution liquid is about 1 to 30% by weight, preferably about 5 to 25% by weight, and more preferably about 10 to 20% by weight, generally speaking.

As the drug-support (drug-supporter, drug-holder, matrix) constituting an interface for iontophoresis, use may be made of non-gel member (hereinafter may simply be referred to as "porous body") which is capable of making contact with a skin, holding (retaining) or supporting a drug, and has a porous or capillary structure through which the drug can be permeated. Such porous body includes organic porous bodies (e.g. fibrous aggregates made from cellulose and other naturally-occurring fibers, a cellulose acetate and other semisynthetic fibers, polyethylene, polypropylene, nylon, polyester and other synthetic fibers, paper and other sheets, a woven or nonwoven fabric and other fabrics, a porous polypropylene, a porous polystyrene, a porous poly(methyl methacrylate), a porous nylon, a porous polysulfone, a porous fluororesin and other porous synthetic resins).

The configuration or shape of the porous body is not particularly restricted, and the porous body may practically be in the form of a sheet. The thickness of the sheet-like porous body can liberally be selected according to the retaining (holding) amount of the drug, and is for example about 1 to 500 μm, and preferably about 10 to 200 μm. The porous body may be a unde-formable body, but it may practically have flexibility.

The area of the sheet-like porous body may suitably be selected from a range depending on the holding amount of the drug, and is about 1 to 10 $cm^2$ and preferably about 2 to 8 $cm^2$, for instance.

The pore size of the sheet-like porous body may be liberally selected within a range not interfering with the holding amount and releasability of the drug, and the mean pore size is, for example, about 0.01 to 20 μm, preferably about 0.1 to 20 μm (e.g. about 0.2 to 20 μm) and practically about 1 to 10 μm.

The application of the interface comprising a non-gel porous body holding or supporting a drug to a surface to make contact with a skin, the drug can be absorbed transdermally with high effectiveness and reproducibility through the matrix (porous body) by dissolving the drug with the drug dissolution liquid.

The drug to be administered through the interface is not particularly limited as far as being transdermally or percutaneously absorbable and being water-soluble, and various physiologically active peptides or proteins or nucleic acids, or non-peptide physiologically active compounds of a low molecular weight can be employed. The molecular weight of the physiologically active peptide or protein or nucleic acid is, for instance, about 100 to 30,000, preferably about 200 to 20,000, more preferably about 500 to 10,000 and practically about 500 to 8,000). The molecular weight of the non-peptide physiologically active compound with a low molecular weight is not greater than about 1,000 (e.g. about 100 to 1,000).

As the physiologically active peptide, there may be mentioned, for example, the following peptides: Luteinizing hormone-releasing hormone (LH-RH), derivatives each having a similar function or activity to LH-RH, such as nafarelin and a polypeptide shown by the following formula (I):

$$\text{(Pyr) Glu-}R^1\text{-Trp-Ser-}R^2\text{-}R^3\text{-}R^4\text{-Arg-Pro-}R^5 \qquad \text{(I)}$$

wherein $R^1$ represents His, Tyr, Trp or p-$NH_2$-Phe, $R^2$ represents Tyr or Phe, $R^3$ indicates Gly or a D-amino acid residue, $R^4$ denotes Leu, Ile or Nle, $R^5$ represents Gly-NH—$R^6$, where $R^6$ denotes a hydrogen atom or a lower alkyl group which may have a hydroxyl group, or NH—$R^6$, where $R^6$ has the same meaning as above, or a salt thereof [see U.S. Pat. No. 3,853,837, U.S. Pat. No. 4,008,209, U.S. Pat. No. 3,972,859, British Patent No. 1423083, Proceedings of the National Academy of Science, 78, 6509–6512 (1981)].

As examples of the D-amino acid residue shown by $R^3$ in the formula (I), there may be mentioned α-D-amino acid having 9 carbon atoms or less (e.g. D-Leu, Ile, Nle, Val, Nval, Abu, Phe, Phg, Ser, Thr, Met, Ala, Trp, α-Aibu). These amino acids may have a protective group (e.g. t-butyl, t-butoxy or t-butoxycarbonyl group). The lower alkyl group shown by $R^6$ includes, for example, alkyl groups each having about 1 to 6 carbon atoms (e.g. methyl, ethyl, propyl, isopropyl, butyl and t-butyl groups).

Incidentally, a salt (e.g. a salt with an acid) or metallic complex compound of the peptide shown by the formula (I) can also be used in the similar manner as the peptide of the formula (I).

Among the polypeptides shown by the formula (I), a polypeptide (TAP-144) wherein $R^1$=His, $R^2$=Tyr, $R^3$=D-Leu, $R^4$=Leu and $R^5$=$NHCH_2$—$CH_3$ is preferably employed.

LH-RH antagonists such as a polypeptide shown by the following formula (II):

$$\text{N-α-t-butoxycarbonyl-O-benzyl-Ser-Trp-Ser-Tyr-}X_1\text{-Leu-Arg-Pro-GlyNH}_2 \qquad \text{(II)}$$

wherein $X_1$ represents D-Ser or D-Trp, or a salt thereof [see U.S. Pat. Nos. 4,086,219, 4,124,577, 4,253,997, and 4,317,815].

Snake poison (venom) peptides each having antagonistic activity against GPIIb/IIIa, such as barbourin, peptides having Arg-Gly-Asp sequence, such as Arg-Gly-Asp-Ser, Gly-Arg-Gly-Asp-Ser-Pro, SK&F-106760 (cyclo-S,S-[AcCys ($N^{\alpha}$-methyl)Arg-Gly-D-Asn-penicillamine]-$NH_2$), and other peptide-like compounds having a similar function or activity, such as (S)-4-[(4-amidinobenzoyl)glycyl]-3-methoxy-carbonylmethyl-2-oxopiperazine-1-acetic acid, (S)-4-(4-guanidinobenzoylamino)acetyl-3-[3-(4-guanidinobenzoylamino)]propyl-2-oxopiperazine-1-acetic acid hydrochloride, MK-383 (2-S-(n-butylsulfonylamino)-3-[4-(N-piperidin-4-yl)butyloxyphenyl)]-propionic acid-HCl), L-700462 (L-Tyr-N-(butylsulfonyl)-O-[4-(piperidinyl)butyl]mono-hydrochloride), SC-56484 (ethyl [[4-(aminoiminomethyl)phenyl]amino]-1,4-dioxybutyl] amino-4-pentinoate), Ro-44-9883 ([1-[N-(p-amidinophenyl)-L-Tyr]-4-piperidinyl]acetic acid), DMP728 (cyclic [D-2-aminobutylyl-N-2-methyl-L-Arg-Gly-L-Asp-3-aminomethyl-benzoic acid]methanesulfonate.

Insulin; somatostatin, somatostatin derivatives, such as a polypeptide shown by the following formula (III):

(III)

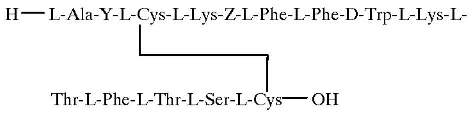

wherein Y represents D-Ala, D-Ser or D-Val, Z represents Asn or Ala, or a salt thereof [see U.S. Pat. Nos. 4,087,390, 4,093,574, 4,100,117 and 4,253,998], growth hormone, growth hormone-releasing hormone; prolactin; adrenocorticotropic hormone (ACTH); melanocyte-stimulating hormone (MSH); thyroid stimulating hormone-releasing hormone (TRH), and derivatives thereof, such as a compound shown by the following formula (IV):

(IV)

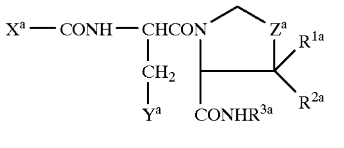

wherein $X^a$ represents a 4- to 6-membered heterocyclic group, $Y^a$ denotes imidazol-4-yl or 4-hydroxylphenyl group, $Z^a$ represents $CH_2$ or S, $R^{1a}$ and $R^{2a}$ independently represent a hydrogen atom or a lower alkyl group, and $R^{3a}$ represents a hydrogen atom or an optionally substituted aralkyl group, or a salt thereof [see Japanese Patent Application Laid-open No. 121273/1975 (JP-A-50-121273), Japanese Patent Application Laid-open No. 116465/1977 (JP-A-52-116465)].

Enkephalin, enkephalin derivatives, such as a peptide shown by the following formula (VII):

(VII)

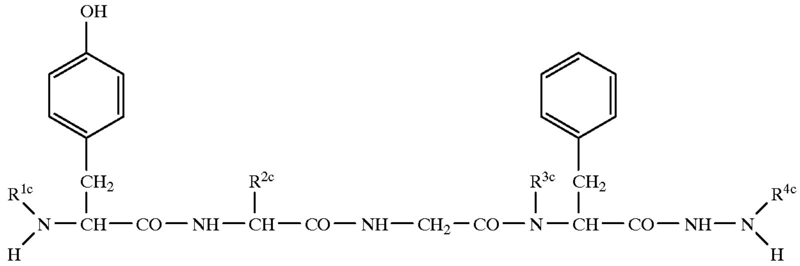

wherein $R^{1c}$ and $R^{3c}$ respectively represent a hydrogen atom or an alkyl group having 1 to 6 carbon atoms, $R^{2c}$ represents a hydrogen atom or a residue of a D-α-amino acid, $R^{4c}$ denotes a hydrogen atom or an optionally substituted aliphatic acyl group having 1 to 8 carbon atoms, or a salt thereof (see U.S. Pat. No. 4,277,394, European Patent Application Laid-open No. 31567 (EP-A-31567)) and other oligopeptides and endorphins.

Thyroid stimulating hormone (TSH); luteinizing hormone (LH); follicle-stimulating hormone (FSH); parathyroid hormone (PTH), derivatives each having a similar function or activity to the parathyroid hormone, such as a peptide shown by the following formula (V)

$R^{1b}$-Val-Ser-Glu-Leu-$R^{2b}$-His-Asn-$R^{3b}$-$R^{4b}$-$R^{5b}$-His-Leu-Asn-Ser-$R^{6b}$-$R^{7b}$-Arg-$R^{8b}$-Glu-$R^{9b}$-Leu-$R^{10b}$-$R^{11b}$-$R^{12b}$-Leu-Gln-Asp-Val-His-Asn-$R^{13b}$ (V)

wherein $R^{1b}$ represents Ser or Aib, $R^{2b}$ represents Met or a naturally-occurring fat-soluble amino acid, $R^{3b}$ denotes Leu, Ser, Lys or an aromatic amino acid, $R^{4b}$ represents Gly or a D-amino acid, $R^{5b}$ denotes Lys or Leu, $R^{6b}$ represents Met or a naturally-occurring fat-soluble amino acid, $R^{7b}$ denotes Glu or a basic amino acid, $R^{8b}$ represents Val or a basic amino acid, $R^{9b}$ represents Trp or 2-(1,3-dithiolan-2-yl)Tyr, $R^{10b}$ denotes Arg or His, $R^{11b}$ represents Lys or His, $R^{12b}$ denotes Lys, Gln or Leu, and $R^{13b}$ represents Phe or Phe-$NH_2$, or a salt thereof [see Japanese Patent Application Laid-open No. 32696/1993 (JP-A-5-32696), Japanese Patent Application Laid-open No. 247034/1992 (JP-A-4-247034), EP-A-510662, EP-A-477885, EP-A-539491], a peptide fragment of the N-terminus (1→34-position) of a human PTH (hereinafter referred to as hPTH (1→34) [G. W. Tregear et al., Endocrinology, 93, 1349–1353 (1973)]; vasopressin, vasopressin derivatives {desmopressin [see Journal of Society of Endocrinology, Japan, 54, No. 5, 676–691 (1978)]}.

Oxytocin; calcitonin, derivatives each having a similar function to calcitonin, such as a compound shown by the following formula (VI):

(VI)

Cys-Ser-Asn-Leu-Ser-Thr-$X^b$-Val-Leu-Gly-Lys-Leu-Ser-Gln-Glu-Leu-His-Lys-Leu-Gln-Thr-Tyr-Pro-Arg-Thr-Asp-Val-Gly-Ala-Gly-Thr-Pro wherein $X^b$ represents 2-aminosberic acid, or a salt thereof [Endocrinology, 1992, 131/6 (2885–2890)]; glucagon; gastrins; secretin; pancreozymin; cholecystokinin; angiotensin; human placental lactogen; human chorionic gonadotropin (HCG).

Kyotorphine; interferons (α-, β-, γ-interferons); interleukins (e.g. interleukins I to XI); tuftsin; thymopoietin; thymostimulin; thymus humoral factor (THF); factor of thymus in serum (FTS) and their derivatives, such as a peptide shown by the following formula (VIII):

PGlu-$X^d$-Lys-Ser-Gln-$Y^d$-$Z^d$-Ser-Asn-OH (VIII)

wherein $X^d$ represents L- or D-Ala, $Y^d$ and $Z^d$ independently represent Gly or a D-amino acid residue having 3 to 9 carbon atoms, or a salt thereof (see U.S. Pat. No. 4,229,438); and other thymus hormones [e.g. thymocin $\alpha_1$ and β4, thymic factor X, etc. "Journal of Clinical Experimental Medicine (IGAKU NO AYUMI)" 125, No. 10, 835–843 (1983)].

Tumor necrosis factor (TNF); colony stimulating factor (CSF); motilin; dynorphin; bombesin; neurotensin; cerulein; bradykinin; urokinase; asparaginase; kallikrein; substance P; nerve growth factor; factor VIII and factor IX of blood coagulation factors; lysozyme chloride; polymyxin B; colistin; gramicidin; bacitracin; protein synthesis-stimulating peptide (British Patent No. 8232082); gastric inhibitory polypeptide (GIP); vasoactive intestinal polypeptide (VIP);

platelet-derived growth factor (PDGF); growth hormone-releasing factor (GRF, somatoclinine, etc.); born morphogenetic protein (BMP); epithelium growth factor (EGF); preprocortistatin (Nature, 381, 242–245 (1996)), erythropoietin and so on.

These physiologically active peptides may be human peptides, or peptides derived from other animals such as bovines, swine, chickens, salmon, eel and so forth. Further, the peptide may be a chimera of a human peptide and a peptide derived from the above animal, or an active derivative in which a part of the structure of the peptide has been changed. By way of an example, the insulin may be an insulin derived from a swine. As to the calcitonin, use may be made of a calcitonin derived from a swine, a chicken, salmon, or eel, or a peptide which is a chimera of a human and salmon and is shown by the following formula (IX) [Endocrinology, 1992, 131/6 (2885–2890)]:

Cys-Gly-Asn-Leu-Ser-Thr-Cys-Met-Leu-Gly-Lys-Leu-Ser-Gln-Glu-Leu-His-Lys-Leu-Gln-Thr-Tyr-Pro-Arg-Thr-Asn-Thr-Gly-Ser-Gly-Thr-Pro (IX)

Preferred examples of the drug include physiologically active peptides and their derivatives, such as a calcitonin, adrenocorticotropic hormone, parathyroid hormone (PTH), hPTH (1→34), insulins, secretin, oxytocin, angiotensin, β-endorphin, glucagon, vasopressin, somatostatin, gastrins, luteinizing hormone-releasing hormone, enkephalins, neurotensin, atrial natriuretic peptide, growth hormone, growth hormone-releasing hormone, bradykinin, substance P, dynorphin, thyroid stimulating hormone, prolactin, interferons, interleukins, GCSF, glutathioperoxidase, superoxide dismutase, desmopressin, somatomedin, endothelin, and their salts. Further, nucleic acids, nucleo-tides and various antigenic proteins may also be employed.

The salt of the physiologically active peptide or its derivative includes, for instance, a salt with an inorganic acid such as hydrochloric acid, sulfuric acid, hydrobromic acid and phosphoric acid; a salt with an organic acid such as formic acid, acetic acid, propionic acid, glycolic acid, oxalic acid, succinic acid, tartaric acid, citric acid, benzenesulfonic acid and p-toluenesulfonic acid; a complex salt with an inorganic compound such as calcium and magnesium.

The nonpeptide physiologically active compound includes compounds each having a molecular weight of about 1,000 or less and having pharmacological activity. The species of the nonpeptide physiologically active compound is not particularly limited, and as the compound, there may be mentioned for example antibiotics, antimycosis (antifungal drugs), hypolipidermic drugs, circulatory drugs, vasoconstrictors, antiplatelet drugs, antitumor drugs, antipyretic, analgesic and/or antiinflammatory agents, antitussive-expectorant agents, sedatives, muscle relaxants, antiepileptic drugs, antiulcer drugs, antidepressant agents, antiallergic agents, cardiotonics, antiarrhythmic agents, vasodilators, hypotensive-diuretic agents, drugs for diabetes, anticoagulants, hemostatic agents, antituberculosis drugs, hormones, narcotic antagonists, bone resorption-inhibitory agents, osteogenetic promoting agents, angiogenesis inhibitors and so forth.

The antibiotic includes, for instance, gentamycin, lividomycin, sisomycin, tetracycline hydrochloride, ampicillin, cefalothin, cefotiam, cefazolin, tienamycin, sulfazecin and so on.

The antifungal agent includes, for example, 2-[(1R,2R)-2-(2,4-difluorophenyl-2-hydroxy-1-methyl-3-(1H-1,2,4-triazol-1-yl)propyl]-4-[4-(2,2,3,3-tetrafluoropropoxy)phenyl]-3(2H,4H)-1,2,4-triazolone, 1-[(1R,2R)-2-(2-fluorophenyl)-2-hydroxy-1-methyl-3-(1H-1,2,4-triazol-1-yl)propyl]-3-[4-(2,2,3,3-tetrafluoropropoxy)phenyl]-2-imidazolidinone and the like.

Examples of the vasoconstrictors include prostaglandin $E_2$ and prostaglandin F.

Examples of the hypolipidermic drug (antihyperlipidermic drug) inlcude paravastatin and simvastatin. The circulatory drug inlcuds delapril hydrochloride, for instance.

As the antiplatelet drug, there may be mentioned, for example, ticlopidine, cilostazol, limaprostat, aspirin and the like.

The antitumor drug (antineoplastic agent) includes, for instance, bleomycin hydrochloride, actinomycin-D, mitomycin-C, adriamycin and fluorouracil.

As examples of the antipyretic, analgesic and/or antiinflammatory agent, there may be mentioned sodium salicylate, sulpyrine, indomethacin sodium, hydromorphone, morphine hydrochloride, fentanyl, buprenorphine and so forth.

The antitussive/expectorant agent includes, for example, ephedrine hydrochloride, codeine phosphate and picoperidamine hydrochloride.

As the sedative, there may be mentioned chlorpromazine hydrochloride, and atropine sulfate, for instance. Examples of the muscle relaxant are pridinol methanesulfonate, tubocurarine chloride and so on.

As the antiepileptic agent, there may be mentioned for instance phenytoin sodium, ethosuximide and so forth. The antiulcer drug includes, for example, metoclopramide. As the antidepressant, there may be mentioned for instance imipramine and phenelzine sulfate.

Examples of the antiallergic drug are diphenhydramine hydrochloride, tripelennamine hydrochloride, clemizole hydrochloride and the like.

As the cardiotonic, there may be mentioned trans-π-oxocamphor and theophyllol, for example. The antiarrhythmic agent includes, for instance, propranolol hydrochloride and oxprenolol hydrochloride. Examples of the vasodilator include oxyfedrine hydrochloride, tolazoline hydrochloride, bamethan sulfate and so forth. The hypotensive-diuretic agent includes, for instance, pentolinium, hexamethonium bromide and so on.

Examples of the antidiabetic agent (hypoglycemic drug) include glymidine sodium, glipizide, metformin, pioglitazone, Troglitazone and the like. As the anticoagulant, use may be made of sodium citrate, for example.

The hemostatic includes menadione sodium bisulfite, acetomenaphtone and tranexamic acid, typically speaking. As the antituberculosis drug, there may be mentioned, for example, isoniazid and ethambutol.

Examples of the hormone drug include β-estradiol, testosterone, prednisolone succinate, dexamethasone sodium sulfate, methimazole and so forth. The narcotic antagonist includes, for example, levalorphan tartrate and nalorphine hydrochloride. As example of the bone resorption inhibitory drug, there may be mentioned (sulfur-containing alkyl)aminomethylene bisphophoate.

Examples of the osteogenetic promoting agents include (2R,4S)-(−)-N-[4-(diethoxyphosphorylmethyl)phenyl]-1,2,4,5-tetrahydro-4-methyl-7,8-methylenedioxy-5-oxo-3-benzothiepine-2-carboxamide.

As the angiogenesis inhibitor, there may be mentioned, for instance, a vascularization inhibitory steroid [see Science 221, 719 (1983)], fumagillol derivatives, [e.g. 0-monochloroacetyl-carbamoylfumagillol, O-dichloroacetylcarbamoylfumagillol (see EP-A-357061, EP-A-359036, EP-A-386667 and EP-A-4152943)].

The drug may be held or supported by the drug holder (porous body) by dissolving the drug in a distilled water for injection, a physiological saline for injection or the like to give an aqueous solution, and applying the solution to the drug holder in a conventional manner such as impregnation, spraying, application, dropwise-adding or the like, and drying the resultant. When the drug is the physiologically active peptide or protein, a dissacharide (e.g. trehalose, maltose, mannitol and inositol) may be added to the aqueous solution containing the drug for improvement of stability of the drug in dry conditions. The proportion of the dissacharide is, for example, about 0.1 to 10 mg/ml, and preferably about 1 to 5 mg/ml (e.g. about 1 to 4 mg/ml).

Long-term preservation of the drug held or supported by the matrix (drug holder or drug retainer) with maintaining activities of the drug can be effected by storing the drug in dry condition. More concretely, preservation of the drug in dry condition may be conducted by, for instance, a process which comprises efficiently drying the drug holder holding the drug, and packaging the drug holder with a film having a small water permeability (e.g. an aluminum film) by vacuum sealing method. Further, in order to retain the dry condition with certainty, the drug holder supporting the drug may be vacuum-sealed and packaged together with a desiccating agent or dryer (e.g. a zeolite-based desiccator such as “SELAM” manufactured by Tokai Chemical Industries, Ltd., a silica gel-based desiccator, etc.). When the drug is to be oxidatively decomposed, an oxygen absorbent (e.g. “AGELESS” manufactured by Mitsubishi Gas Chemical Co., Ltd.) may be incorporated into the package in addition to the desiccating agent.

The holding amount of the drug relative to the matrix (drug holder) may only be an effective amount according to the species of the drug, species of the drug holder, area or portion to be administered, and is, for example, about 0.1 to 100 $\mu$g, and preferably about 0.5 to 50 $\mu$g (e.g. about 1 to 50 $\mu$g) per 1 $cm^2$ of the sheet-like drug holder.

In the present invention, the interface for iontophoresis may be composed of the porous matrix holding or supporting the drug as mentioned above, or it may be composed of the porous matrix holding or supporting the drug, and the humectant held or supported by the porous matrix.

Incidentally, the drug is not necessarily held by the sheet-like matrix (e.g. a holder in the form of a membrane), and a solution containing the drug may be injected into the holder or neighborhood of the holder. In such a case, the interface may also be composed of the matrix and the humectant held or supported by the matrix. The drug may be incorporated into the dissolution liquid, that is, the dissolution liquid may contain the humectant and the drug.

Furthermore, a suitable adsorption inhibitor may be incorporated into the dissolution liquid for dissolving the drug in order to ensure further inhibition of loss of the physiologically active peptide or protein due to adsorption. The adsorption inhibitor includes, for instance, an albumin (e.g. a bovine serum albumin (BSA), a human serum albumin (HSA) and other serum albumins), gelatin and other water soluble proteins; alkylbenzenesulfonic acid salts (e.g. a sodium salt) and other anionic surfactants, a $C_{8-20}$ alkyltrimethylammonium chloride, a $C_{8-20}$ alkyltrimethylammonium chloride, a $C_{8-20}$ alkylbenzyldimethylammonium chloride (benzalkonium chloride, hereinafter sometimes referred to as BAC), a 4-$C_{1-10}$ alkylphenyloxyethoxyethylbenzyldimethylammonium chloride (e.g. benzethonium chloride) and other cationic surfactants, Tween 80 and other nonionic surfactants, and alkali metal salts (e.g. sodium chloride) and the like. The amount of the adsorption inhibitor may for example be about 0.00001 to 1% (w/w), preferably about 0.0001 to 0.5% (w/w), and more preferably about 0.001 to 0.1% (w/w) based on the amount of the dissolution liquid. Further, an appropriate absorption accelerator (e.g. monoterpene, aliphatic monoglyceride, Azone (manufactured by Nelson), limonen, oleic acid, lauric acid, octanol) may be incorporated into the drug dissolution liquid. The content of the absorption accelerator is, for instance, about 0.1 to 80% (w/w), preferably about 0.5 to 50% (w/w), and more preferably about 1 to 30% (w/w) based on the amount of the dissolution liquid.

The interface composed of the drug holder (porous body) is useful for transdermal drug delivery (endermic drug administration) by iontophoresis with the use of a variety of applicator which is applicable to a skin. The applicator is provided with an electrode to which an electric voltage is applicable, and an interface which is conductible to the electrode, capable of making contact with a skin, and holds or supports the drug. The applicator is capable of being supplied with an aqueous solution, for dissolving the drug, containing the humctant. The transdermal drug delivery system of the invention comprises an interface composed of the matrix (in particular the sheet-like porous body), the humectant-containing dissolution liquid for dissolving the drug, and a supply means for supplying the dissolution liquid to the interface. The drug dissolved with the dissolution liquid is transdermally or endermically absorbed by means of iontophoresis. FIG. 1 is a cross sectional view illustrating an embodiment of the applicator comprising the interface.

The applicator shown in FIG. 1 is provided with a support (base member) 4 having flexibility and being formed with an opening 9, and a container (reservoir) 3 disposed in a part corresponding to the opening 9. The container is provided with an electrode 1 such as a silver electrode, and accommodates electric conductor 2 such as an electric conductive nonwoven fabric or sponge containing water or an electric conductive gel such as a water-containing gel, poly(vinyl alcohol) (PVA) comprising NaCl. The electric conductor 2 may comprise a porous sponge or nonwoven fabric containing an aqueous solution comprising a hydrophilic substance with water retentivity. In the part of the under portion of the support 4 corresponding to the opening 9 are disposed an ion exchange membrane 5, the inner surface of which faces to the electric conductor 2, and an interface 6 as laminated by means of an adhesive tape 7. The adhesive tape 7 is utilized for attaching the applicator to the skin. The electric conductor 2 of the container 3 is conductible to the electrode 1 and capable of making contact with the ion exchange membrane 5 and interface 6 through the opening 9. Further, an injection port 10 capable of injecting a liquid is formed between the ion exchange membrane 5 and the interface 6.

When such an applicator is used in a case where the interface holds or supports the drug, a nozzle tip of an injection tip 8 may be inserted to the injection port 10 between the ion exchange membrane 5 and the interface 6 to inject the drug dissolution liquid such as a distilled water for injection containing the humectant. When the interface does not hold or support the drug, a solution containing the drug and the drug dissolution liquid containing the humectant may be respectively injected to the interface 6, and in a case that the interface holds or supports both the drug and the humectant, the drug dissolution liquid such as a distilled water for injection may only be injected to the interface 6.

The amount of the drug dissolution liquid to be injected may be selected from a range according to the size of the applicator, the surface area of the interface and the holding amount of the drug, and usually is about 30 to 500 μl and preferably about 50 to 200 μl.

Incidentally, in the support of the applicator, a second container (reservoir) as a reservoir for reservation of a liquid for drug dissolution such as a distilled water for injection may be disposed in the opening distant from the first container, and an interface may be laminated, through a nonwoven fabric disposed in the area from the first container toward the second container, on the outer surface of the ion exchange membrane. When such applicator is used, the second container may be pierced by, for example inserting a needle through the second container and the support to form a pore in the support connecting to the inside of the second container, so that the liquid for dissolution of the drug or drug-containing solution is permeated to the nonwoven fabric for dissolution of the drug held by the interface or for supplying the drug-containing solution to the interface.

The first and second containers can be formed by, for instance polyethylene or other synthetic resins. As the ion exchange membrane, use may be made of various membranes each having ion exchange capability, such as "AC220 Membrane" (trade name) manufactured by Asahi Chemical Industries, Japan. As the nonwoven fabric, a variety of nonwoven fabrics through which a liquid is permeable, such as "Benberg Half" (trade name) manufactured by Asahi Chemical Industries, Japan, can be used. As the adhesive tape, use may be made of a variety of adhesive tapes each having adhesive properties with respect to a skin, such as "Blenderm" (trade name) manufactured by 3M Pharmaceuticals, M.N. (Minnesota).

For the purpose of inhibiting or suppressing transpiration or dissipation of moisture not only from the interface but also from the skin, and hence improving electric conductivity by means of the humectant in the drug dissolution liquid in the delivery process or transdermal delivery system with the use of the above applicator, the drug dissolution liquid is required to diffuse through the matrix (drug holder) to the skin. It is effective to hold or support the humectant at least in an area to which the electric current is applied in order to restrain transpiration or dissipation of moisture and to administer the drug effectively. In this system, transdermal absorption (delivery) of the drug by means of the interface for iontophoresis can be promoted by holding or supporting the drug and the humectant at least in an area of the interface to which electric current is applied. In particular, when moisture is supplemented by, for example, a single supply of the humectant-containing dissolution liquid, and hence the humectant is held or supported in the area to which the electric current is applied, electric conductivity can be maintained with inhibiting transpiration or dissipation of moisture over a long period. Therefore, when the drug is delivered or administered by means of plural electric current applications, such a complicated operation is not required as to supply the drug dissolution liquid such as a distilled water plural times in order to supply the moisture in succeeding current application step. Especially, use of the amino acid or its salt as the humectant ensures inhibition of transpiration or dissipation of the moisture even in a small amount and mitigates skin irritation accompanied with the current application, so that it is useful for transdermal drug delivery by means of iontophoresis.

The transdermal delivery (endermic administration) of the drug by means of iontophoresis can be effected by applying an electric current to the electrode of the applicator and a reference electrode to pass an electricity. As the electric current voltage, an alternating current voltage may be employed but use is practically made of a direct current voltage. As such direct current voltage, not only a continuous direct current voltage but also a depolarized direct current pulse voltage can be utilized. Preferably, use may be made of an electric power supply which can apply a depolarizing pulse direct current voltage, in particular, a square pulse direct current voltage. The frequency of the pulse direct current voltage may be selected within a range of, for example, about 0.1 to 200 kHz, preferably about 1 to 100 kHz and more preferably about 5 to 80 kHz. The ON/OFF ratio of the pulse direct current voltage is, for instance, about 1/100 to 20/1, preferably about 1/50 to 15/1 and more preferably about 1/30 to 10/1. The applied voltage may be selected from a range not injuring a skin of a living body and not adversely affecting the transdermal absorption ratio, and is, for instance, about 1 to 20 V, and preferably about 3 to 15 V. The current application time is, for example in continuous application of the current, not longer than 24 hours, preferably not longer than 12 hours and in particular not longer than 6 hours.

The present invention, where the drug dissolution liquid containing the humectant is used, provides inhibition of transpiration of the moisture from the drug dissolution liquid and hence ensures long-period retention of electric conductivity in the drug delivery system with the use of iontophoresis. Accordingly, the invention provides effective and certain transdermal absorption of the drug held in the interface, and is useful for transdermal delivery of the drug with high bioavailability and excellent reproducibility. Further, the use of the amino acid or its salt as the humectant mitigates skin irritation accompanied with application of electric current, and hence is useful for transdermal drug delivery by means of iontophoresis.

The following examples are intended to illustrate the present invention in more detail, but should by no means limit the scope of the invention.

EXAMPLES

Comparative Example 1

An abdominal skin of a male SD rat (7-week aged) was clipped with a hair clipper and treated with a shaver under pentobarbital-anesthetization, and was cleaned with an absorbent cotton containing a 70% aqueous solution of ethanol for defatting and disinfection.

In the iontophoresis was used an applicator illustrated in FIG. 1. That is, the drug holder (Biodyne Plus Membrane, Nihon Pall Ltd., Japan; 2.5 $cm^2$) was previously dipped in a 10% (w/v) bovine serum albumin (BSA) and dried to hold or possess 40 μg of hPTH (1→34) per membrane in dry condition and thereby an interface for iontophoresis was obtained. This interface was applied and fixed to the abdominal skin of the rat. After application of the interface to the skin, the dried drug was dissolved by supplying 120 μl of a distilled water from an injection tip 8 to the interface. The electric current application was effected by using a pulse direct current electric voltage of a direct-current 12-V constant voltage with a frequency of 40 kHz and an ON/OFF ratio of 3/7, and repeating three times a combination of 15-minutes current application and 5-minute-non-current application. This current application pattern was repeated three times with an interval of 2 hours. After a predetermined time lapse, blood was took from jugular veins (cervical vein) of the rat and centrifuged at a rate of 12,000 rpm for 10 minutes to give a serum sample. The concentration (pg/ml) of the hPTH (1→34) in the serum was determined by radioimmunoassay method. The results are illustrated in FIG. 2. In FIG. 2, long narrow boxes in axis of abscissa (time) represent electric current application time.

Comparative Example 2

The hPTH (1→34) was transdermally administered in the same manner as Comparative Example 1 using the same interface for iontophoresis, administration process, conditions of current application and determination method of serum hPTH (1→34) concentration, except that 60 μl of a distilled water was supplied from the injection tip 8 immediately before the second and third current application cycles respectively. The results are set forth in FIG. 2.

Example 1

The hPTH (1→34) was administered in the same interface for iontophoresis, administration process, conditions for current application and determination method of the serum hPTH (1→34) concentration as Comparative Example 1 except that 120 μl of a 30% (w/w) glycerin aqueous solution in lieu of the distilled water was injected once after adhesion of the interface. The results are shown in FIG. 2.

As apparent from FIG. 2, in the single supply of the distilled water (Comparative Example 1), third peak corresponding to the numbers of the current application cycles was not found, to the contrary, in the single supply of the 30% (w/w) glycerin aqueous solution (Example 1), three peaks corresponding to the current application cycles were found, equaling to the three times-supply of the distilled water (Comparative Example 2). The bioavailability (BA) was evaluated from the ratio of the area under the serum hPTH concentration-time curve (AUC value) of the tested group relative to the AUC value obtained by intravenous administration on same dose basis [actual intravenous dose, 2 μg/kg of hPTH (1→34)]. The BA was 17.8%, 9.0% and 13.8% for Example 1, Comparative Example 1 and Comparative Example 2 respectively. Thus, the single supply of 30% (w/w) aqueous solution of glycerin provides an equal absorptivity to the three times supply of the distilled water.

Example 2

By conducting a single injection of 120 μl of a 10% (w/w) aqueous solution of glycerin in lieu of the distilled water after application of the interface, the hPTH (1→34) was transdermally delivered in the same manner as Comparative Example 1 employing the same interface for iontophoresis, administration process and conditions for current application.

In the single supply of the 10% (w/w) aqueous solution of glycerin (Example 2), the bioavailability (BA) was 9.5%, as evaluated from the ratio of the area under the serum hPTH concentration-time curve (AUC value) of the tested group relative to the AUC value obtained by intravenous administration on same dose basis [actual intravenous dose, 2 μg/kg of hPTH (1→34)].

Example 3

Except that single injection of 120 μl of a 60% (w/w) aqueous solution of glycerin in lieu of the distilled water was conducted after application of the interface, the hPTH (1→34) was transdermally administered employing the same interface for iontophoresis, administration process and conditions of current application as Comparative Example 1.

In the single supply of the 60% (w/w) aqueous solution of glycerin (Example 3), the bioavailability (BA) was 18.5%, as evaluated from the ratio of the area under the serum hPTH concentration-time curve (AUC value) of the tested group relative to the AUC value obtained by intravenous administration on same dose basis [actual intravenous dose, 2 μg/kg of hPTH (1→34)].

Example 4

The hPTH (1→34) was transdermally administered in the same interface for iontophoresis, administration process and conditions for current application as Comparative Example 1, except that 120 μl of a 30% (w/w) aqueous solution of proline was once injected, instead of the distilled water, after application of the interface by using the same interface for iontophoresis, administration process and conditions for current application as Comparative Example 1. The results are illustrated in FIG. 3. The results of Comparative Example 2 are also shown in FIG. 3. In FIG. 3, narrow and long boxes in the axis of abscissa (time) denote current application time (period).

As clearly shown in FIG. 3, similar blood concentration pattern to Example 1 was obtained by a single supply of the 30% (w/w) aqueous solution of proline, and the bioavailability (BA) was 17.6% as evaluated from the ratio of the area under the serum hPTH concentration-time curve (AUC value) of the tested group relative to the AUC value obtained by intravenous administration on same dose basis [actual intravenous dose, 2 μg/kg of hPTH (1→34)].

Example 5

Except that 120 μl of a 10% (w/w) aqueous solution of proline in lieu of the 30% (w/w) aqueous solution of proline was injected after application of the interface, the hPTH (1→34) was transdermally administered employing the same interface for iontophoresis, administration process and conditions of current application as Example 4. The results are set forth in FIG. 4. As apparent from FIG. 4, the single supply of the 10% (w/w) aqueous solution of proline provide a similar pattern of the hPTH (1→34) in serum to Example 1, and BA was 17.8%.

Example 6

Figure 4:
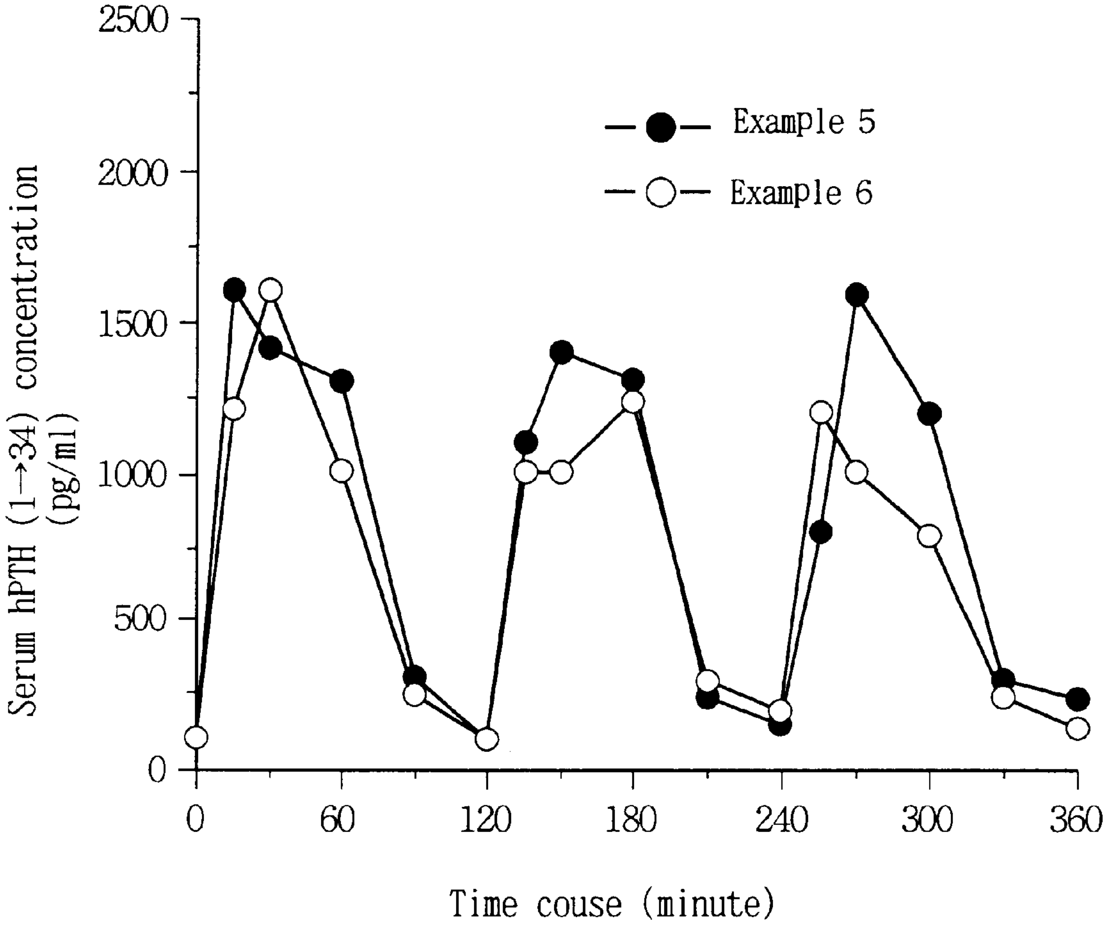
FIG. 4 is a graph showing changes of the serum hPTH (1→34) concentration during the time course (time passage) in Example 5 and Example 6.

The hPTH (1→34) was transdermally administered by employing the same interface for iontophoresis, administration process and conditions of current application as Example 4, except that 120 μl of 10% (w/w) aqueous solution of sodium pyroglutamate was injected in lieu of the 30% (w/w) aqueous solution of proline after application of the interface. The results are shown in FIG. 4. As clearly illustrated in FIG. 4, a single supply of the 10% (w/w) aqueous solution of sodium pyroglutamate resulted in a similar pattern of the hPTH (1→34) in blood to Example 1, and BA was 15.2%.

What is claimed is:

1. A dissolution liquid for transdermal drug delivery by iontophoresis with the use of an interface composed of a porous matrix holding or supporting a drug, wherein the dissolution liquid comprises water and selected from the group consisting of polyhydric alcohols having 2 to 4 hydroxyl groups per molecule, sugar alcohols, amino acids and an amino acid as a humectant.

2. A dissolution liquid as claimed in claim 1, wherein the amino acid has a nitrogen-containing heterocycle.

3. A dissolution liquid as claimed in claim 1, wherein the amino acid has a non-aromatic nitrogen-containing 5-membered heterocycle.

4. A dissolution liquid as claimed in claim 1, wherein the amino acid is proline or hydroxyproline.

5. A dissolution liquid as claimed in claim 1, wherein the concentration of the amino acid is 1 to 30% by weight.

6. A dissolution liquid as claimed in claim 1, wherein the drug is (1) a physiologically active peptide or protein, or (2) a nonpeptide physiologically active compound.

7. A dissolution liquid as claimed in claim 1, wherein the drug is (1) a physiologically active peptide or protein with a molecular weight of 100 to 30,000, or (2) a nonpeptide physiologically active compound with a molecular weight of 100 to 1,000.

8. A dissolution liquid as claimed in claim 1, wherein the dissolution liquid is a liquid for dissolving a physiologically active peptide or protein with a molecular weight of 100 to 30,000 being held or supported by a matrix, and comprises an aqueous solution containing an amino acid as a humectant in a proportion of 1 to 50% by weight.

9. A dissolution liquid for transdermal drug delivery by iontophoresis with the use of an interface composed of a porous matrix, wherein the dissolution liquid comprises water, an amino acid as a humectant and a drug.

10. An interface for iontophoresis which comprises a porous matrix holding or supporting a drug and the dissolution liquid as claimed in claim 1.

11. A transdermal drug delivery system which is provided with an interface capable of making contact with a skin and comprising a matrix holding or supporting a drug, the dissolution liquid as claimed in claim 1, and a supply means for supplying the dissolution liquid to the interface, wherein the drug dissolved with the dissolution liquid is transdermally derived by means of iontophoresis.

12. A transdermal drug delivery system as claimed in claim 11, wherein the matrix is a porous nongel matrix in the form of a sheet.

13. A transdermal drug delivery system as claimed in claim 11, wherein the amino acid is held or supported at least in an area to which an electric current is applied.

14. An applicator comprising an electrode, to which an electric voltage is applicable, and the interface as claimed in claim 10 being conductible to the electrode, capable of making contact with a skin.

15. A method for promoting transdermal absorption of a drug by means of an interface for iontophoresis, which comprises holding or supporting a drug and the dissolution liquid as claimed in claim 1 at least in an area to which an electric current is applied.

16. A transdermal drug delivery process which comprises allowing an interface holding or supporting a drug to make contact with a skin, and dissolving the drug with the dissolution liquid as claim in claim 1.

* * * * *

UNITED STATES PATENT AND TRADEMARK OFFICE

CERTIFICATE OF CORRECTION

PATENT NO. : 5,993,848

DATED : November 30, 1999

INVENTOR(S) : Yasuyuki SUZUKI et al.

It is certified that error appears in the above-identified patent and that said Letters Patent is hereby corrected as shown below:

In claim 1, delete the folowing:

-- selected from the group consisting of polyhydric alcohols having 2 to 4 hydroxyl groups per molecule, sugar alcohols, amino acids and --

Signed and Sealed this

Twelfth Day of September, 2000

Attest:

Q. TODD DICKINSON

*Attesting Officer*

*Director of Patents and Trademarks*